United States Patent
Sun et al.

(10) Patent No.: US 8,494,632 B2
(45) Date of Patent: *Jul. 23, 2013

(54) SELF-CALIBRATING RATE-ADAPTIVE PACEMAKER

(75) Inventors: Weimin Sun, Thousand Oaks, CA (US); Bruce R. Jones, Hopkins, MN (US); Douglas J. Lang, Arden Hills, MN (US); Donald L. Hopper, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/230,563

(22) Filed: Sep. 12, 2011

(65) Prior Publication Data

US 2012/0004696 A1    Jan. 5, 2012

Related U.S. Application Data

(63) Continuation of application No. 12/507,414, filed on Jul. 22, 2009, now Pat. No. 8,019,418, which is a continuation of application No. 11/457,382, filed on Jul. 13, 2006, now Pat. No. 7,567,839, which is a continuation of application No. 10/839,875, filed on May 6, 2004, now Pat. No. 7,079,897, which is a continuation of application No. 09/657,402, filed on Sep. 8, 2000, now Pat. No. 6,823,214.

(51) Int. Cl.
   *A61N 1/18*    (2006.01)
(52) U.S. Cl.
   USPC ......................................................... 607/19
(58) Field of Classification Search
   None
   See application file for complete search history.

(56) References Cited

U.S. PATENT DOCUMENTS

| | | | |
|---|---|---|---|
| 4,719,921 A | 1/1988 | Chirife | |
| 4,773,401 A | 9/1988 | Citak et al. | |
| 4,865,036 A | 9/1989 | Chirife | |
| 4,873,980 A | 10/1989 | Schaldach | |
| 4,919,137 A | 4/1990 | Schaldach | |
| 4,926,863 A | 5/1990 | Alt | |
| 4,940,053 A | 7/1990 | Mann et al. | |
| 4,945,909 A | 8/1990 | Fearnot et al. | |
| 5,044,365 A | 9/1991 | Webb et al. | |
| 5,078,133 A | 1/1992 | Heinz et al. | |
| 5,154,171 A | 10/1992 | Chirife | |
| 5,156,147 A | 10/1992 | Warren et al. | |
| 5,168,869 A | 12/1992 | Chirife | |
| 5,170,785 A | 12/1992 | Heinz et al. | |
| 5,174,286 A | 12/1992 | Chirife | |

(Continued)

OTHER PUBLICATIONS

"U.S. Appl. No. 09/638,975, Non Final Office Action mailed Feb. 27, 2002", 9 pages.

(Continued)

*Primary Examiner* — Mark W Bockelman
(74) *Attorney, Agent, or Firm* — Schwegman Lundberg & Woesner, P.A.

(57) ABSTRACT

A system and method for automatically adjusting the operating parameters of a rate-adaptive cardiac pacemaker. In accordance with the method, maximum exertion levels attained by the patient are measured at periodic intervals and stored. The stored maximum exertion levels may then be used to update a long-term maximal exertion level, and the slope of the rate-response curve is adjusted to map the updated long-term maximal exertion level to a maximum allowable pacing rate. The stored maximum exertion levels may also be used to update a sensor target rate which is used to adjust the slope of the rate response curve.

20 Claims, 7 Drawing Sheets

U.S. PATENT DOCUMENTS

| | | | |
|---|---|---|---|
| 5,179,949 | A | 1/1993 | Chirife |
| 5,197,467 | A | 3/1993 | Steinhaus et al. |
| 5,226,413 | A | 7/1993 | Bennett et al. |
| 5,249,572 | A | 10/1993 | Bonnet |
| 5,303,702 | A | 4/1994 | Bonnet et al. |
| 5,376,106 | A | 12/1994 | Stahmann et al. |
| 5,423,870 | A | 6/1995 | Olive et al. |
| 5,487,753 | A | 1/1996 | MacCarter et al. |
| 5,562,711 | A | 10/1996 | Yerich et al. |
| 5,645,575 | A | 7/1997 | Stangl et al. |
| 5,674,257 | A | 10/1997 | Stroebel et al. |
| 5,792,195 | A | 8/1998 | Carlson et al. |
| 5,792,198 | A | 8/1998 | Nappholz |
| 5,931,858 | A | 8/1999 | Kadhiresan et al. |
| 5,967,083 | A | 10/1999 | Kleinsasser |
| 5,974,340 | A | 10/1999 | Kadhiresan |
| 5,976,083 | A | 11/1999 | Richardson et al. |
| 6,055,454 | A | 4/2000 | Heemels |
| 6,119,040 | A | 9/2000 | Chirife |
| 6,273,856 | B1 | 8/2001 | Sun et al. |
| 6,411,850 | B1 | 6/2002 | Kay et al. |
| 6,490,485 | B1 | 12/2002 | Sun et al. |
| 6,509,588 | B1 | 1/2003 | O'Phelan et al. |
| 6,519,495 | B1 | 2/2003 | Sun et al. |
| 6,522,525 | B1 | 2/2003 | O'Phelan et al. |
| 6,571,126 | B1 | 5/2003 | O'Phelan et al. |
| 6,674,634 | B2 | 1/2004 | O'Phelan et al. |
| 6,684,102 | B1 | 1/2004 | O'Phelan et al. |
| 6,687,118 | B1 | 2/2004 | O'Phelan et al. |
| 6,699,265 | B1 | 3/2004 | O'Phelan et al. |
| 6,709,946 | B2 | 3/2004 | O'Phelan et al. |
| 6,736,759 | B1 | 5/2004 | Stubbs et al. |
| 6,823,214 | B1 | 11/2004 | Sun et al. |
| 6,839,593 | B1 | 1/2005 | Sun et al. |
| 6,990,375 | B2 | 1/2006 | Kloss et al. |
| 7,079,897 | B2 | 7/2006 | Sun et al. |
| 7,092,758 | B2 | 8/2006 | Sun et al. |
| 7,493,163 | B2 | 2/2009 | Sun et al. |
| 7,567,839 | B2 | 7/2009 | Sun et al. |
| 8,019,418 | B2 | 9/2011 | Sun et al. |
| 2006/0247704 | A1 | 11/2006 | Sun et al. |
| 2006/0265019 | A1 | 11/2006 | Sun et al. |

OTHER PUBLICATIONS

"U.S. Appl. No. 09/638,975, Notice of Allowance mailed Sep. 9, 2002", 5 pages.

"U.S. Appl. No. 09/638,975, Response filed Jun. 27, 2002 to Non-Final Office Action mailed Feb. 27, 2002", 8 pages.

"U.S. Appl. No. 09/657,402, Notice of Allowance mailed Jun. 14, 2004", 7 pages.

"U.S. Appl. No. 09/657,402, Notice of Allowance mailed Dec. 23, 2003", 5 pages.

"U.S. Appl. No. 09/657,402, Response filed Nov. 3, 2003 to Restriction Requirement mailed Oct. 3, 2003", 1 page.

"U.S. Appl. No. 09/657,402, Restriction Requirement mailed Oct. 3, 2003", 4 pages.

"U.S. Appl. No. 10/364,129, Non-Final Office Action mailed Oct. 19, 2005", 13 pages.

"U.S. Appl. No. 10/364,129, Notice of Allowance mailed Mar. 22, 2006", 6 pages.

"U.S. Appl. No. 10/364,129, Response filed Feb. 21, 2006 to Non-Final Office Action mailed Oct. 19, 2005", 10 pages.

"U.S. Appl. No. 10/839,875, Non-Final Office Action mailed Nov. 3, 2005", 4 pages.

"U.S. Appl. No. 10/839,875, Notice of Allowance filed Feb. 22, 2006", 4 pages.

"U.S. Appl. No. 10/839,875, Preliminary Amendment filed May 6, 2004", 4 pages.

"U.S. Appl. No. 10/839,875, Preliminary Amendment filed May 24, 2005", 10 pages.

"U.S. Appl. No. 10/839,875, Response filed Jan. 25, 2006 to Non-Final Office Action mailed Nov. 3, 2005", 8 pages.

"U.S. Appl. No. 11/457,382, Non-Final Office Action mailed Oct. 8, 2008", 4 pages.

"U.S. Appl. No. 11/457,382, Notice of Allowance mailed Mar. 23, 2009", 4 pages.

"U.S. Appl. No. 11/457,382, Response filed Jan. 6, 2009 to Non-Final Office Action mailed Oct. 8, 2008", 8 pages.

"U.S. Appl. No. 11/461,632, Non-Final Office Action mailed Mar. 17, 2008", 11 pages.

"U.S. Appl. No. 11/461,632, Notice of Allowance mailed Oct. 8, 2008", 6 pages.

"U.S. Appl. No. 11/461,632, Response filed Jun. 17, 2008 to Non-Final Office Action mailed Mar. 17, 2008", 11 pages.

"U.S. Appl. No. 11/461,632, Supplemental Notice of Allowability mailed Jan. 9, 2009", 2 pages.

"U.S. Appl. No. 12/507,414, Non Final Office Action mailed Dec. 27, 2010", 4 pages.

"U.S. Appl. No. 12/507,414, Notice of Allowance mailed May 13, 2011", 5 pages.

"U.S. Appl. No. 12/507,414, Response filed Mar. 28, 2011 to Non Final Office Action mailed Dec. 27, 2010", 9 pages.

Benditt, D. G, et al., "Sensor-Triggered, Rate-Variable Cardiac Pacing", Annals of Internal Medicine, 107(5), (1987), 714-724.

Soucie, L. P., et al., "Correlation of the Heart Rate-Minute Ventilation Relationship with Clinical Data: Relevance to Rate-Adaptive Pacing.", Pacing and Clinical Electrophysiology, 20(8, Part 1), (1997), 1913-1918.

Treese, N., et al., "Ventilation and Heart Rate Response During Exercise in Normals: Relevance for Rate Variable Pacing", Pacing and Clinical Electrophysiology, 16, (1990), 1693-1700.

SELF-CALIBRATING RATE-ADAPTIVE PACEMAKER

CLAIM OF PRIORITY

This application is a continuation of U.S. patent application Ser. No. 12/507,414, filed on Jul. 22, 2009, now issued as U.S. Pat. No. 8,019,418, which is a continuation of U.S. patent application Ser. No. 11/457,382, filed on Jul. 13, 2006, now issued as U.S. Pat. No. 7,567,839, which is a continuation of U.S. patent application Ser. No. 10/839,875, filed on May 6, 2004, now issued as U.S. Pat. No. 7,079,897, which is a continuation of U.S. patent application Ser. No. 09/657,402, filed on Sep. 8, 2000, now issued as U.S. Pat. No. 6,823,214, the specifications of which are incorporated herein by reference.

FIELD OF THE INVENTION

This invention pertains to systems and methods for cardiac rhythm management. In particular, the invention relates to a system and method for automatically adjusting the operating parameters of a rate-adaptive cardiac pacemaker.

BACKGROUND

A conventional cardiac pacemaker is an implantable battery-powered electronic device that responds to sensed cardiac events and elapsed time intervals by changing its functional states so as to properly interpret sensed data and deliver pacing pulses to the heart at appropriate times. The pacing pulses are delivered through a lead made up of electrodes on a catheter or wire that connects the pacemaker to the heart. Some electronic devices, called implantable cardioverter-defibrillators, are capable of delivering electrical shocks, rather than small-intensity pacing stimuli, in order to cardiovert or defibrillate the heart. The term "pacemaker" as used herein, however, should be taken to mean both pacemakers and any device with a pacemaking function, such as an implantable cardioverter/defibrillator with a pacemaker incorporated therein.

Pacemakers can generally operate in a variety of modes, generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers, which are the primary subject of the present invention, are called rate-adaptive pacemakers and are designated by a fourth letter added to the three-letter code, R.

The most common condition for which pacemakers are used is the treatment of bradycardia. Permanent pacing for bradycardia is indicated in patients with symptomatic bradycardia of any type as long as it is likely to be permanent or recurrent and is not associated with a transient condition from which the patient may recover. Atrio-ventricular conduction defects (i.e., AV block) that are fixed or intermittent and sick sinus syndrome represent the most common indications for permanent pacing. In chronotropically competent patients in need of ventricular pacing, atrial triggered modes such as DDD or VDD are desirable because they allow the pacing to track the physiologically normal atrial rhythm, which causes cardiac output to be responsive to the metabolic needs of the body. Atrial triggering modes are contraindicated, however, in patients prone to atrial fibrillation or flutter or in whom a reliable atrial sense cannot be obtained. In the former case, the ventricles will be paced at too high a rate. Failing to sense an atrial P wave, on the other hand, results in a loss of atrial tracking which can lead to negative hemodynamic effects because the pacemaker then reverts to its minimum ventricular pacing rate. In pacemaker patients who are chronotropically incompetent (e.g., sinus node dysfunction) or in whom atrial-triggered modes such as DDD and VDD are contraindicated, the heart rate is dictated solely by the pacemaker in the absence of faster intrinsic cardiac activity. That pacing rate is determined by the programmed escape intervals of the pacemaker and is referred to as the lower rate limit or LRL.

Pacing the heart at a fixed rate as determined by the LRL setting of the pacemaker, however, does not allow the heart rate to increase with increased metabolic demand. Cardiac output is determined by two factors, the stroke volume and heart rate, with the latter being the primary determinant. Although stroke volume can be increased during exercise (e.g., due to increased venous return and increased myocardial contractility), the resulting increase in cardiac output is usually not sufficient to meet the body's metabolic needs unless the heart rate is also increased. If the heart is paced at a constant rate, as for example by a VVI pacemaker, severe limitations are imposed upon the patient with respect to lifestyle and activities. It is to overcome these limitations and improve the quality of life of such patients that rate-adaptive pacemakers have been developed.

The body's normal regulatory mechanisms act so as to increase cardiac output when the metabolic rate is increased due to an increased exertion level in order to transport more oxygen and remove more waste products. One way to control the rate of a pacemaker, therefore, is to measure the metabolic rate of the body and vary the pacing rate in accordance with the measurement. Metabolic rate can effectively be directly measured by, for example, sensing blood pH or blood oxygen saturation. Practical problems with implementing pacemakers controlled by such direct measurements, however, have led to the development of pacemakers that are rate-controlled in accordance with physiological variables that are indirectly reflective of the body's metabolic rate such as body temperature or respiratory rate. (See, e.g., U.S. Pat. No. 5,376,106 issued to Stahmann et al. and assigned to Cardiac Pacemakers, Inc., the disclosure of which is hereby incorporated by reference.) Measuring respiratory rate, for example, estimates oxygen consumption. A better approximation to oxygen consumption is the minute ventilation, however, which is the product of ventilation rate and tidal volume. An even more indirect measurement of metabolic rate is the measurement of body activity or motion with either an accelerometer or vibration sensor. The activity-sensing pacemaker uses an accelerometer or microphone-like sensor inside the pacemaker case that responds to motion or mechanical vibrations of the body by producing electrical signals proportional to the patient's level of physical activity. More complex rate-responsive systems incorporate multiple sensors that compensate for the deficits of specific individual sensors. All of the above-mentioned sensors, however, are for the purpose of ascertaining the exertion level of the patient and changing the heart rate in accordance therewith.

In such rate-adaptive pacemakers that vary the pacing rate in accordance with a measured exertion level, the control system is generally implemented as an open-loop controller that maps a particular exertion level to one particular heart rate, termed the sensor-indicated rate (SIR). Various parameters are set in order to fit the control system to the individual patient, including minimal and maximal heart rate and responsiveness. Minimal and maximal heart rate settings are primarily for patient safety, and the responsiveness of the pacemaker determines how much change in heart rate results from a given change in exertion level. An under-responsive pacemaker will unnecessarily limit exercise duration and intensity in the patient because the heart rate will not increase enough to match metabolic demand, while an over-responsive pacemaker will lead to palpitations and patient discomfort. Control parameters are generally set in conventional rate-adaptive pacemakers after implantation and during clinical visits according to a fixed formula or as a result of exercise testing. There is a need for rate-adaptive pacemakers that automatically adjust control parameters in accordance with a patient's changing physical condition so as to reduce the need for follow-up clinical visits and extensive testing.

SUMMARY OF THE INVENTION

The present invention relates to a system and method for automatically adjusting the responsiveness of a rate-adaptive pacemaker using exertion level measurements. In a particular implementation of the pacemaker, measured exertion levels in the patient are mapped to a pacing rate by a dual-slope rate response curve. The slope of the rate-response curve changes at a specified heart rate breakpoint from a low-rate response value to a high-rate response value, termed the low rate response factor and high rate response factor, respectively. The heart rate breakpoint may be computed as a percentage of the patient's rate reserve, which is the difference between the maximum and minimum pacing rates as defined by the rate response curve. In accordance with the invention, maximum exertion levels attained by the patient during a day (or other specified period) are collected and used to dynamically adjust the responsiveness of the pacemaker.

In one embodiment, daily maximum exertion levels and daily maximum sensor indicated rates are collected and averaged over a specified period, such as one week. A sensor target rate representing the heart rate demand corresponding to the averaged daily maximum exertion level is then computed as a function of the daily maximum exertion level and the patient's maximum exercise capacity as defined by a long-term maximum exertion level. Periodically, (e.g., every week) the responsiveness of the pacemaker is increased or decreased in accordance with whether the weekly average maximum sensor indicated rate is lesser or greater, respectively, than the sensor target rate by adjusting the slope of the rate response curve. The slope of the rate response curve may be adjusted by incrementing or decrementing the low rate response factor by a specified step size and then adjusting the high rate response factor to map the patient's long-term maximum exertion level to the maximum sensor indicated rate.

In another embodiment, daily maximum exertion levels are collected for a specified time period and used to update the long-term maximum exertion level. The slope of the rate response curve is then adjusted in order for the updated long-term maximum exertion level to be mapped to a specified maximum sensor indicated rate. In the case of a dual-slope rate response curve, the curve may be adjusted with the heart rate breakpoint maintained as a fixed percentage of the rate reserve or as a dynamic percentage of the rate reserve that changes in accordance with changes in the long-term maximum exertion level. In the latter case, the rate response curve may be adjusted such that the percentage of the patient's rate reserve used to compute the heart rate breakpoint is increased or decreased by the percentage increase or decrease, respectively, in the long-term maximum exertion level as a result of updating.

DESCRIPTION OF SPECIFIC EMBODIMENTS

Figure 1A:
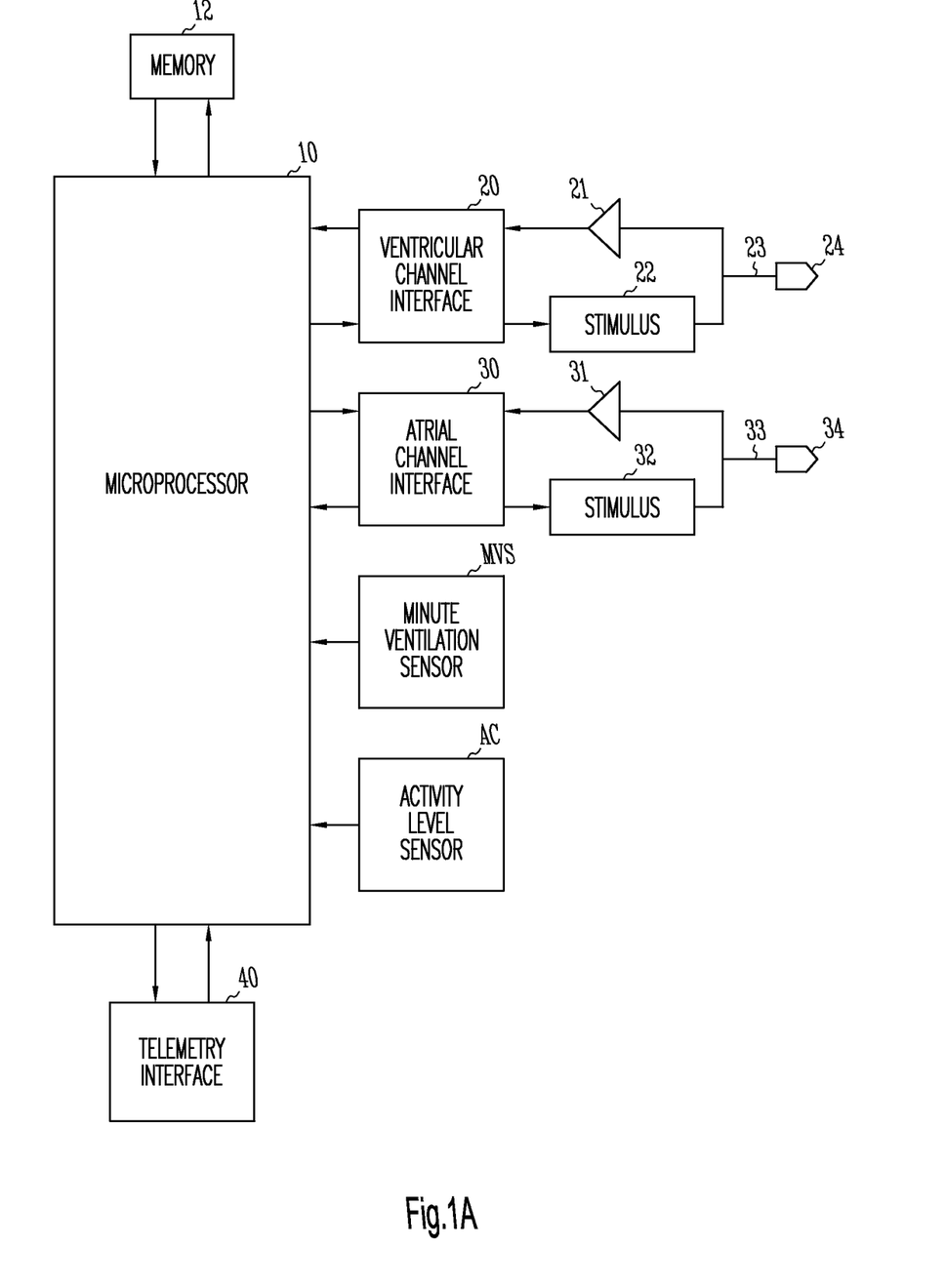
FIG. 1A is a block diagram of a rate-adaptive pacemaker.

A particular implementation of a rate-adaptive pacemaker as shown in FIG. 1A. As used herein, the term pacemaker should be taken to mean any cardiac rhythm management device with a pacing functionality including an implantable cardioverter/defibrillator that includes a pacemaker. A pacemaker controller senses cardiac events through a sensing channel and outputs pacing pulses to the heart via a pacing channel in accordance with a programmed pacing mode. A microprocessor serves as the controller in this embodiment and communicates with a memory 12 via a bidirectional data bus 13. The memory 12 typically comprises a ROM or RAM for program storage and a RAM for data storage. The pacemaker has atrial sensing and pacing channels comprising electrode 34, lead 33, sensing amplifier 31, pulse generator 32, and an atrial channel interface 30 which communicates bidirectionally with a port of microprocessor 10. The device also has ventricular sensing and pacing channels comprising electrodes 24, leads, sensing amplifier 21, pulse generator 22, and ventricular channel interface 20. For each channel, the same lead and electrode are used for both sensing and pacing. The channel interfaces 20 and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. A telemetry interface 40 is also provided for communicating with an external programmer. A minute ventilation sensor MVS and an accelerometer AC are employed to sense the minute ventilation and body activity, respectively. The pacemaker uses the sensed minute ventilation and/or the accelerometer signal to adjust the rate at which the pacemaker paces the heart in the absence of a faster intrinsic rhythm. The microprocessor 10 executes programmed instructions that implement various pacing and rate-adaptive algorithms, including the method described below.

Figure 1B:
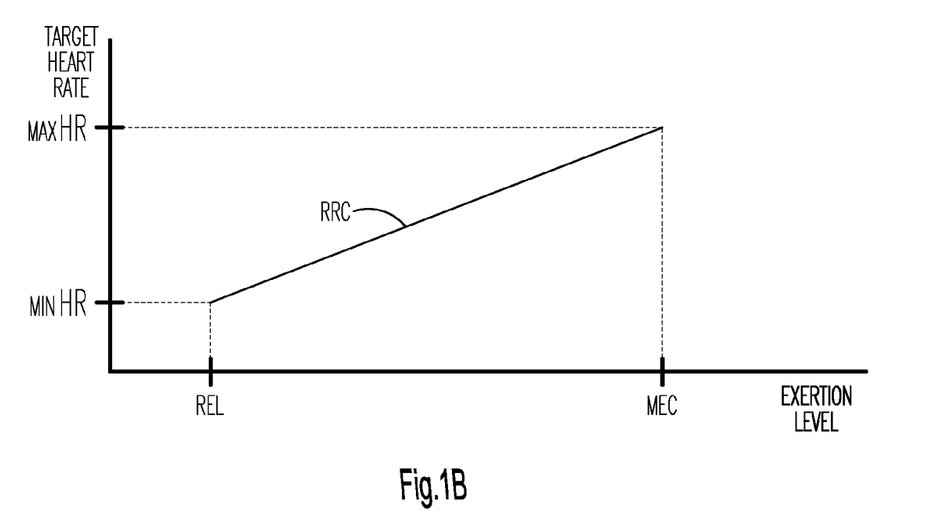
FIG. 1B is a diagram of a single-slope rate response curve.

The responsiveness of a rate-adaptive pacemaker is controlled in accordance with a rate-response curve RRC such as shown in FIG. 1B. Other embodiments may use a dual-slope curve or a non-linear curve. A change in exertion level as determined from a minute ventilation measurement causes a proportional change in the sensor indicated rate in accordance with the slope of the curve, termed the response factor RF. The sensor indicated rate is then used as a lower rate limit (LRL) by the pacemaker to pace the heart in accordance with a programmed pacing mode. The LRL is the rate at which the heart is paced in the absence of faster intrinsic activity. As shown in the figure, the rate response curve maps a resting exertion level REL to a minimum sensor indicated rate MinHR which corresponds to the minimum LRL that is to be used by the pacemaker. The maximum sensor indicated rate MaxHR is the maximum rate at which the pacemaker is allowed to pace the heart and is mapped to by the rate response curve from the maximum exertion level the patient is expected to be able to reach, referred to as the maximum exercise capacity MEC. In the single-slope rate response curve shown in FIG. 1B, the response factor RF may then be defined as:

RF=(MaxHR−MinHR)/(MEC−REL).

Figure 3:
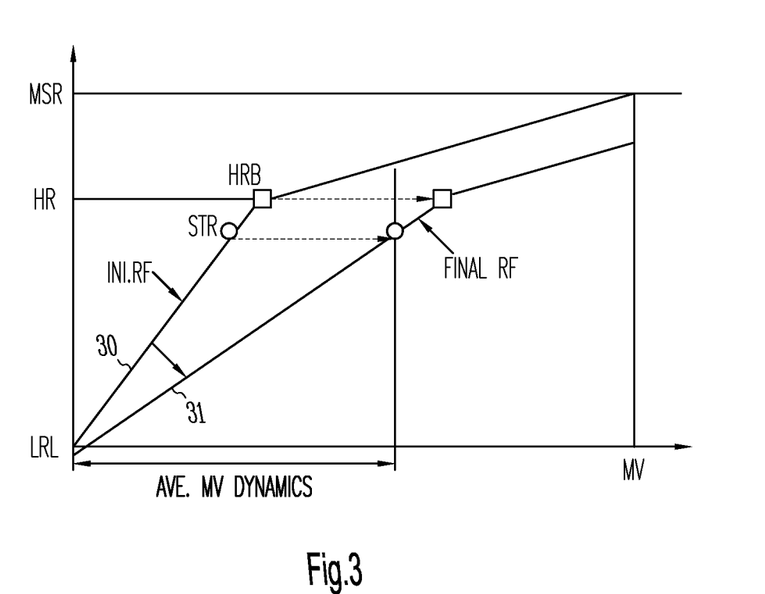
FIG. 3 shows the slope change of the rate response curve in response to changes in the average sensor indicated rate.

The responsiveness of the pacemaker can also be controlled in accordance with a dual-slope rate response curve such as shown in FIG. 3. A change in exertion level EXL (as determined from either minute ventilation or body activity) causes a change in the sensor indicated rate that is proportional to the slope of the response curve. The slope of the rate response curve is designated the initial response factor RF below the heart rate breakpoint HRB, and designated the high rate response factor HRRF above HRB. The heart rate breakpoint HRB ideally should be set to correspond to an exertion level equal to the anaerobic threshold AT of the patient. The anaerobic threshold is the level of exertion above which the concentration of lactic acid produced by anaerobic metabolism starts to build up rapidly in the blood. It thus represents an exertion level at which the body starts to utilize oxygen less efficiently and, along with maximal oxygen consumption, is a useful index of current physical conditioning. The responsiveness of the pacemaker below the anaerobic threshold as defined by RF is greater than that above the threshold as defined by HRRF so that overpacing above the anaerobic threshold is avoided.

The endpoints of any rate response curve are defined by a long-term maximum exertion level $EXL_{LongTermMax}$ corresponding the patient's maximum exercise capacity which is mapped to the maximum sensor indicated rate MSR, and a minimum exertion level $EXL_{Min}$ corresponding to a null EXL signal (i.e., rest) which is mapped to the minimum LRL. The minimum LRL is equal to the lower rate limit LRL setting of pacemaker with no rate adaptation.

The initial values of the parameters RF, HRRF, HRB, long-term maximum exertion level $EXL_{LongTermMax}$, and maximum sensor indicated rate MSR can be specified at the time of pacemaker implant. The initial long-term maximum exertion level is set to the exertion level which is mapped to the MSR by the initial rate response curve or set to a value based upon population data with the other parameters adjusted accordingly. The MSR is usually set to be equivalent to the age-predicted maximum heart rate MAR and limits the pacing rate of the pacemaker to protect against excessively rapid pacing, which would be especially detrimental in patients with coronary artery disease. The MSR may therefore in some cases be set to a value lower than the age-predicted maximum heart rate MAR depending upon the patient's medical condition. A sensor target rate STR may also be specified to represent a heart rate demand corresponding to a particular exertion level. The STR is used as a reference by the pacemaker control system to adjust the rate response curve so that the sensor target rate is reached when the patient exercises at the particular exertion level. As described below, the STR may be updated periodically to represent a heart rate demand corresponding to a maximum exertion level attained during a specified period (e.g., daily) and is compared with a maximum sensor indicated rate during the same specified period to adjust the rate response curve.

The initial values of $EXL_{LongTermMax}$ and HRB can be determined from formulas dependent upon the patient's age, while the initial STR can be determined by a formula dependent upon a desired target heart rate during exercise and a specified exercise frequency as prescribed by a physician at the time of implant. These parameters can be left fixed unless reprogrammed by a physician during a follow-up clinical visit, but this method of setting control parameters suffers from a number of limitations. First, the patient's maximum exercise capacity $EXL_{LongTermMax}$ and physiological heart rate at the anaerobic threshold HRB depend not only on age, but also upon the physical conditioning of the patient. Also, the STR and exercise frequency prescribed by the physician may not match the patient's actual exercise activity and metabolic heart rate demand (i.e., the heart rate that results in a cardiac output sufficient to meet metabolic needs). If the STR prescribed at implant is less than the patient's actual metabolic heart rate demand, the patient will only be paced at the prescribed STR and will never reach the required rate. If the STR is greater than the actual metabolic heart rate demand, on the other hand, overpacing will occur. Finally, in the initial setting of the parameters, no account is taken of how the patient's exercise activity and exercise capacity may change over time.

In accordance with the invention, the control system automatically adjusts the STR and $EXL_{LongTermMax}$ from initially set values in accordance with measurements of periodic maximum exertion levels attained by the patient as measured by a minute ventilation or activity sensor. Periodic maximum sensor indicated rates are also collected for comparison with the STR in order to adjust the response factor RF. Such periodic maximum exertion levels and sensor indicated rates are preferably collected on a daily basis, and a weekly average of the daily maximums is then used for weekly parameter adjustment. Other similar time periods for collection, averaging, or updating could, of course, be used in place of the daily and weekly periods referred to in the embodiments described herein, which periods may be referred to as short-term and intermediate-term periods, respectively. In addition, sensor measurements and sensor indicated rates are preferably moving averaged over a specified averaging period (where the averaging period may range, for example, from 30 seconds to 5 minutes) in order to smooth the data and filter out any spurious signals. In a particular embodiment, the exertion level signals EXL are automatically collected by the device and moving averaged over a one minute averaging period. The maximum among the collected moving averages is then set equal to the daily maximum exertion level $EXL_{DailyMax}$, which is registered and stored. The daily maximum sensor indicated rate is similarly determined. The daily maximum exertion level $EXL_{DailyMax}$ can then be averaged over a specified time period with the resulting average maximum exertion level also registered and stored, e.g., on a weekly basis to result in a weekly average value $Week\_Avg(EXL_{DailyMax})$.

The long-term maximum exertion level $EXL_{LongTermMax}$ is updated in accordance with stored measurements of the patient's daily maximum exertion levels at periodic intervals (e.g., every three months, six months, or year). The maximum value among the stored daily maximum exertion levels measured over the specified long-term period is thus registered and stored as $EXL_{LongTermMax}$. The STR is updated weekly based upon the weekly average of the daily maximum exertion levels $EXL_{DailyMax}$ and the current value of $EXL_{LongTermMax}$. Since the STR is automatically adjusted, an initial setting that does not correspond to the patient's true physiological heart rate demand during exercise will be corrected so that the patient will not be locked to an inappropriate rate. The control system can then use the updated STR and/or $EXL_{LongTermMax}$ values to adjust the slope of the rate response curve (i.e., RF and/or HRRF) and the HRB. Automatically adjusting both the rate response curve slope and HRB thus obviates the need for the physician to attempt to calculate the most appropriate parameter values at the time of implantation or during follow-up. The responsiveness of the pacemaker will then be reflective of the patient's individual exertion levels, and will also automatically adjust in response to changes in the patient's functional capacity or level of physical conditioning. The patient's exertion level and exercise capacity history is also stored and able to be retrieved by a clinician in order to assess both the patient and the functioning of the pacemaker.

The STR is determined from an average of daily maximal exertion level heart rates $EXR_{DailyMax}$ over a specified period. The daily maximal exertion level heart rate to $EXR_{DailyMax}$ approximates the heart rate demand corresponding to the daily maximum exertion level $EXL_{DailyMax}$. The daily maximum exertion level heart rate $EXR_{DailyMax}$ is thus a function of the daily maximal exertion level $EXL_{DailyMax}$ and is determined in this embodiment in accordance with the following table that maps ranges of $EXL_{DailyMax}$ values relative to $EXL_{LongTermMax}$ to an $EXR_{DailyMax}$ value expressed relative to the MAR:

| $EXL_{DailyMax}$ | $EXR_{DailyMax}$ (in bpm) |
| --- | --- |
| 80-100% of $EXL_{LongTermMax}$ = | 90% of MAR |
| 50-80% of $EXL_{LongTermMax}$ = | 70% of MAR |
| <50% of $EXL_{LongTermMax}$ = | 90 bpm |

In other embodiments, rather than comparing $EXL_{DailyMax}$ with discrete thresholds of $EXL_{LongTermMax}$, the daily maximum exertion level heart rate $EXR_{DailyMax}$ may be expressed as a continuous function of the daily maximal exertion level $EXL_{DailyMax}$, $EXL_{LongTermMax}$, and the MAR:

$$EXR_{DailyMax} = (EXL_{DailyMax}/EXL_{LongTermMax})MAR$$

In a presently preferred embodiment, the STR is computed as a weekly average of daily maximum exertion level heart rates.

The daily maximum sensor indicated rate SIR is also moving averaged over the same period as the exertion level signals EXL, with the daily maximum moving average value $SIR_{DailyMax}$ being registered and stored. The $SIR_{DailyMax}$ values are averaged in this embodiment on a weekly basis to result in the average maximal sensor indicated rate Week_Avg($SIR_{DailyMax}$). The weekly average maximal sensor indicated rate Week_Avg($SIR_{DailyMax}$) is compared with the STR on a weekly basis to control the adjustment of the response factor RF (i.e., the slope of the rate response curve). If the STR is higher than the Week_Avg($SIR_{DailyMax}$), the RF will be increased by one step; if the STR is lower, the RF will be decreased by one step. The HRRF may then either be updated as a percentage of the RF or in accordance with an updated $EXL_{LongTermMax}$ value.

The HRB is initially set to a value above the LRL equal to 60% of the rate reserve, where the rate reserve is the amount by which a patient's age-predicted maximum heart rate MAR exceeds the LRL. In one embodiment the HRB is maintained as a fixed percentage of the rate reserve as initially set. In another embodiment, the HRB is a dynamic percentage of the rate reserve such that if the long-term maximal exertion level $EXL_{LongTermMax}$ (i.e., the patient's peak exercise capacity) is increased due to exercise or fitness training, the HRB is increased proportionately to the increase in the long-term maximal exertion level. The HRB is thus determined from a formula based upon both the patient's age and peak exertion level, which is more indicative of the patient's actual physiological heart rate demand at the anaerobic threshold than a formula based upon age alone. In an exemplary embodiment, for the first three months after implant the long-term maximal exertion level is started with a value equal to the upper limit of maximal exertion levels measured from a similar patient population, or with a value mapped from the initial RF, HRB, HRRF, and age-predicted maximum heart rate MAR. The initial long-term maximal exertion level $EXL_{LongTermMax}$ is maintained for three months unless updated by a measured $EXL_{DailyMax}$ value that is higher.

Figure 2:
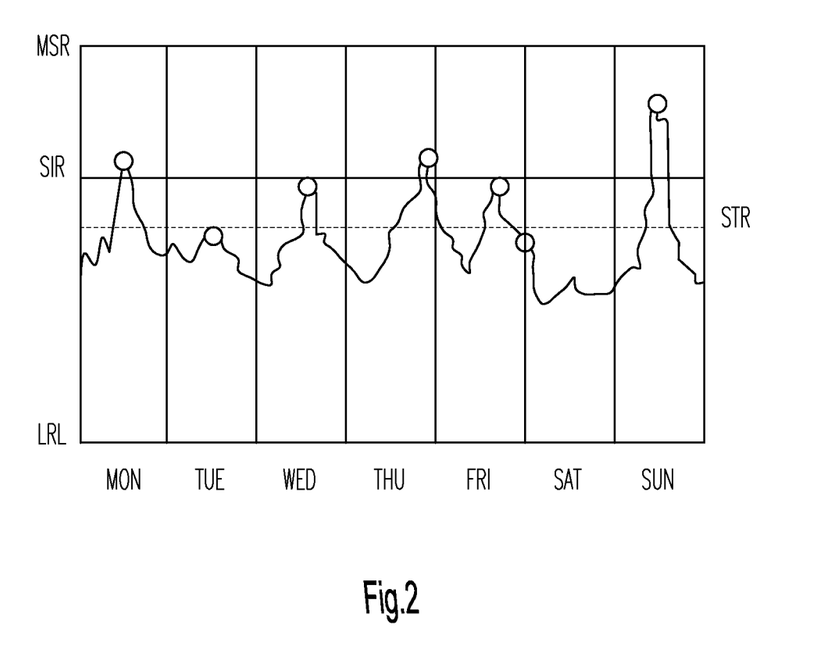
FIG. 2 shows values of $SIR_{DailyMax}$ plotted for each day of the week.

In the specific embodiment detailed below, the STR is periodically adjusted in accordance with updated weekly averages of the daily maximum exertion level heart rate $EXR_{DailyMax}$. The $EXL_{LongTermMax}$ is also updated in accordance with weekly averages of the patient's maximum exertion levels. A minimum value for $EXL_{LongTermMax}$; designated $EXL_{LongTermMaxMin}$, is determined from population data, the rate response function, and the age-predicted maximum heart rate MAR. In this embodiment, the HRB is maintained at the initialized value, and the HRRF is maintained as a constant percentage of the RF. The method steps are divided into three phases: initialization, daily monitoring, and weekly updating:

Initialization:
MSR=(220−age);
MAR=max(220−age, MSR);
LRL=60;
HRB=LRL+0.6*(MAR−LRL)
RF=5 (for a minute ventilation signal MV) or RF=8 (for an activity signal XL);
$EXL_{LongTermMax}$=average maximal exertion value taken from population data;
$EXL_{LongTermMaxMin}$=max (MAR/(1.3*RF), population average minimum value);
HRRF=0.7*RF;

Daily Monitoring:
Compute 1 minute moving averages of EXL and SIR signals and store maximum;
$EXL_{DailyMax}$=maximum moving average value of EXL computed during the day;
$SIR_{DailyMax}$=maximum moving average value of SIR computed during the day;

Weekly Parameter updating:
Compute Week_Avg($SIR_{DailyMax}$) and Week_Avg ($EXL_{DailyMax}$);
$EXL_{LongTermMax}$=max (Week_Avg($EXL_{DailyMax}$) averaged over 3 mos., $EXL_{LongTermMaxMin}$);
STR=($F_{rest}$*90+$F_{mild}$*0.7*MAR+$F_{vigorous}$*0.9*MAR)/7
where $F_{rest}$=(number of days $EXL_{DailyMax}$ is less than 50% of $EXL_{LongTermMax}$)
$F_{mild}$=(number of days $EXL_{DailyMax}$ is between 50% and 80% of $EXL_{LongTermMax}$)
$F_{vigorous}$=(number of days $EXL_{DailyMax}$ is over 80% of $EXL_{LongTermMax}$);
If Week_Avg($SIR_{DailyMax}$)<STR then RF is increased by one step (e.g. 15%);

If Week_Avg($SIR_{DailyMax}$)>STR then RF is decreased by one step (e.g. 15%);
HRRF=0.7*RF;

In addition, an initial optimization procedure may be performed for a specified period (e.g., 6 months) in order to optimize the initial settings of the control parameters used by the algorithm. In a first such optimization procedure, the patient first exercises for a one-hour period with the parameters set as follows:
After first hour:
    $EXL_{LongTermMax}$=max($EXL_{LongTermMaxMin}$, (1+B)* $EXL_{FirstHourMax}$) where $EXL_{FirstHourMax}$ is the maximal exertion level during the hour of exercise and B is a selected buffering factor (e.g., 1, 0.33, or 0);
Every hour:
    If $EXL_{DailyMax}$>$EXL_{LongTermMax}$
    then increase $EXL_{LongTermMaxMin}$ by one step (e.g., 15%);
    RF=(HRB−LRL)/(0.5*$EXL_{LongTermMaxMin}$);
Every week:
    If (1+B)*$EXL_{DailyMax}$<$EXL_{LongTermMax}$ and $EXL_{LongTermMax}$>$EXL_{LongTermMaxMin}$
    then decrease $EXL_{LongTermMaxMin}$ by one step (e.g., 15%);
    RF=(HRB−LRL)/(0.5*$EXL_{LongTermMaxMin}$);

In a second optimization procedure, the following steps are performed with no preceding exercise period:
Initial setting:
    MSR=LRL+0.75*(MAR−LRL);
For second month:
    MSR=LRL+0.90*(MAR−LRL);
For third through sixth months:
    MSR=LRL+(MAR−LRL);
Every hour:
    If $EXL_{DailyMax}$>S*$EXL_{LongTermMax}$
    then increase $EXL_{LongTermMaxMin}$ by one step (e.g., 15%);
    RF=(HRB−LRL)/(0.5*$EXL_{LongTermMaxMin}$);
    where S=85% for first month and 100% for next five months;
Every week:
    If (1+B)*$EXL_{DailyMax}$<$EXL_{LongTermMax}$ and $EXL_{LongTermMax}$>$EXL_{LongTermMaxMin}$
    then decrease $EXL_{LongTermMaxMin}$ by one step (e.g., 15%);
    RF=(HRB−LRL)/(0.5*$EXL_{LongTermMax}$);

In a second specific embodiment, the method steps are similarly divided into three phases: initialization, daily monitoring, and weekly updating.
Initialization:
MAR=(220−age);
LRL=60;
HRB=LRL+0.6*(MAR−LRL);
RF=5 (for a minute ventilation signal MV) or RF=8 (for an activity signal XL);
$EXL_{LongTermMax}$=average maximal exertion value taken from population data;
$EXL_{LongTermMaxMin}$=max (MAR/(1.3*RF), population average minimum value);
HRRF=determined such that $EXL_{LongTermMax}$ maps to MAR;
Daily Monitoring:
Compute 1-3 minute moving averages of EXL and SIR signals and store maximum;
$EXL_{DailyMax}$=maximum moving average value of EXL computed during the day;
$SIR_{DailyMax}$=maximum moving average value of SIR computed during the day;
Weekly parameter updating:
$EXL_{LongTermMax}$=max ($EXL_{DailyMax}$, ($EXL_{LongTermMaxMin}$));
Compute Week_Avg($SIR_{DailyMax}$) and Week_Avg ($EXL_{DailyMax}$);
HRB is adjusted proportionate to the change in $EXL_{LongTermMax}$ such that
    HRB=LRL+(0.6+percentage change in $EXL_{LongTermMax}$)* (MAR−LRL);
STR=($F_{rest}$*90+$F_{mild}$*0.7*MAR+$F_{vigorous}$*0.9*MAR)/7
    where $F_{rest}$=(number of days $EXL_{DailyMax}$ is less than 50% of $EXL_{LongTermMax}$)
    $F_{mild}$=(number of days $EXL_{DailyMax}$ is between 50% and 80% of $EXL_{LongTermMax}$)
    $F_{vigorous}$=(number of days $EXL_{DailyMax}$ is over 80% of $EXL_{LongTermMax}$);
If Week_Avg($SIR_{DailyMax}$)<STR then RF is increased by one step;
If Week_Avg($SIR_{DailyMax}$)>STR then RF is decreased by one step;
HRRF=min (RF, (MAR−HRB)/($EXL_{LongTermMax}$−HRB/RF));
During first 6 months after implant, the following steps are also performed:
If $EXL_{DailyMax}$>$EXL_{LongTermMax}$
    then ($EXL_{LongTermMax}$=1.1*$EXL_{DailyMax}$);
If $EXL_{DailyMax}$>$EXL_{LongTermMax}$
    then $EXL_{LongTermMax}$=max(0.9*$EXL_{LongTermMax}$, Min ($EXL_{LongTermMax}$));

FIGS. 2 through 5 illustrate the operation of the methods just described. FIG. 2 shows values of $SIR_{DailyMax}$ plotted for each day of the week. The average value of $SIR_{DailyMax}$ for the week Week_Avg($SIR_{DailyMax}$) is also shown along with the sensor target rate STR. As can be seen, Week_Avg ($SIR_{DailyMax}$) exceeds the STR, so the slope of the rate response curve RF is reduced by one step. FIG. 3 shows the result of the slope change where curve 30 has adjusted to curve 31. The system has been made less responsive in order to compensate for the average sensor indicated rate exceeding the sensor target rate during the past week. If the Week_Avg ($SIR_{DailyMax}$) had been less than the STR, the slope of the rate responsive curve would have been increased by one step to make the system more responsive. Note that in this example, both STR and HRB are left unchanged, but are mapped to different exertion levels due to the change in slope of the rate response curve. The high rate response factor may be further adjusted to map the patient's long-term maximum exertion level to the specified maximum sensor indicated rate.

Figure 4:
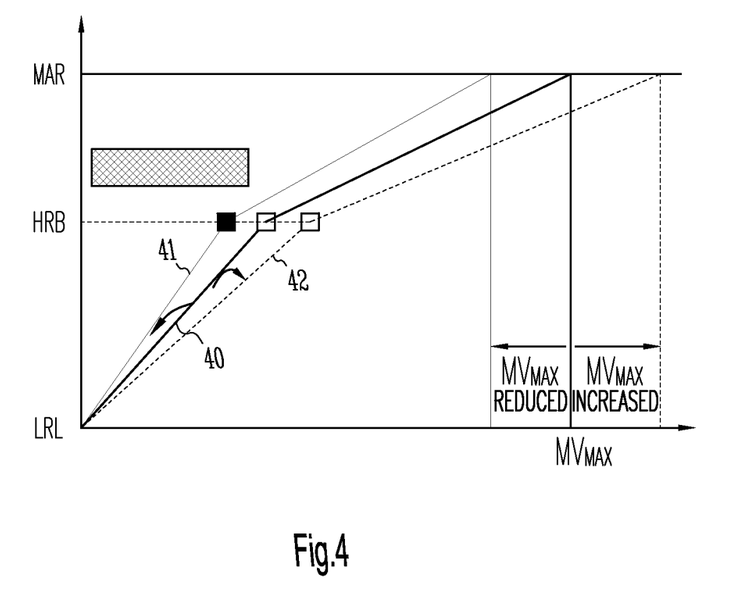
FIGS. 4 and 5 show how changes in the fitness level of the patient change the slope of the rate response curve.
Figure 5:
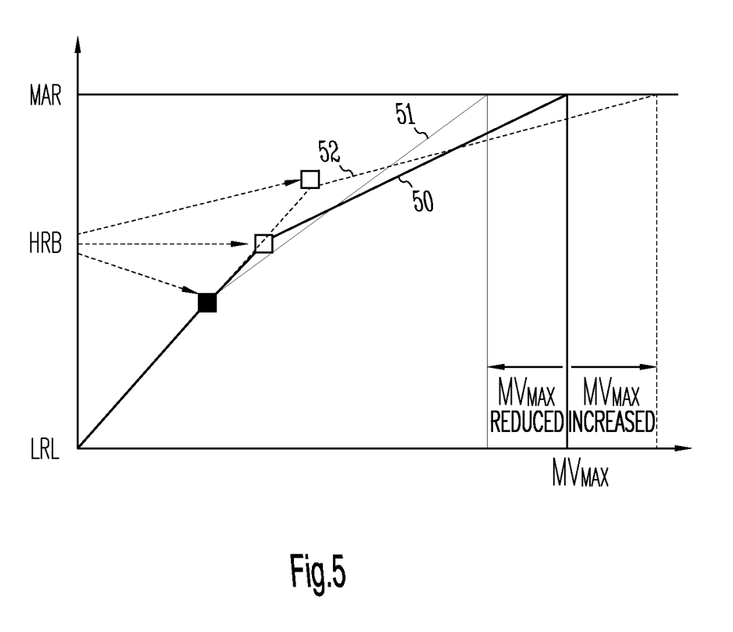

FIGS. 4 and 5 show how the method responds to changes in the fitness level of the patient as reflected by changes in the long-term maximal exertion level $EXL_{LongTermMax}$. The rate response curve is dynamically adjusted in response to changes in $EXL_{LongTermMax}$ by adjusting the curve so that $EXL_{LongTermMax}$ is mapped to the patient's maximum heart rate MAR (or MSR). In FIG. 5, the initial rate response curve 40 is adjusted to curve 41 when the $EXL_{LongTermMax}$ value is decreased, and adjusted to curve 42 when the $EXL_{LongTermMax}$ value is increased. In this example, the heart rate breakpoint HRB is maintained as a constant percentage of the rate reserve and so is left unchanged as $EXL_{LongTermMax}$ changes. FIG. 5 shows how the HRB value may instead be computed as a dynamic percentage of the rate reserve that depends upon the value of $EXL_{LongTermMax}$. As $EXL_{LongTermMax}$ decreases due to deconditioning, initial rate response curve 50 is adjusted to curve 51. The heart rate breakpoint in this embodiment is also adjusted in accordance with the formula given above so that it decreases, which is reflective of the fact that the anaerobic threshold decreases with decreasing fitness levels. Similarly, if $EXL_{LongTermMax}$ is increased due to an increased fitness level, rate response curve 50 adjusts to curve 52, and the HRB parameter increases.

For safety reasons, it may be desirable in certain embodiments to implement the system described above such that $\text{EXL}_{LongTermMax}$ is only increased in response to changes in the patient's physical conditioning and never decreased. That is, once the patient achieves a certain $\text{EXL}_{LongTermMax}$, it is assumed that the patient's maximum exercise capacity will not decrease from that level. This prevents the $\text{EXL}_{LongTermMax}$ from being decreased simply by the patient going for a long period without exercising maximally and thereby subjecting the patient to overpacing.

Figure 6:
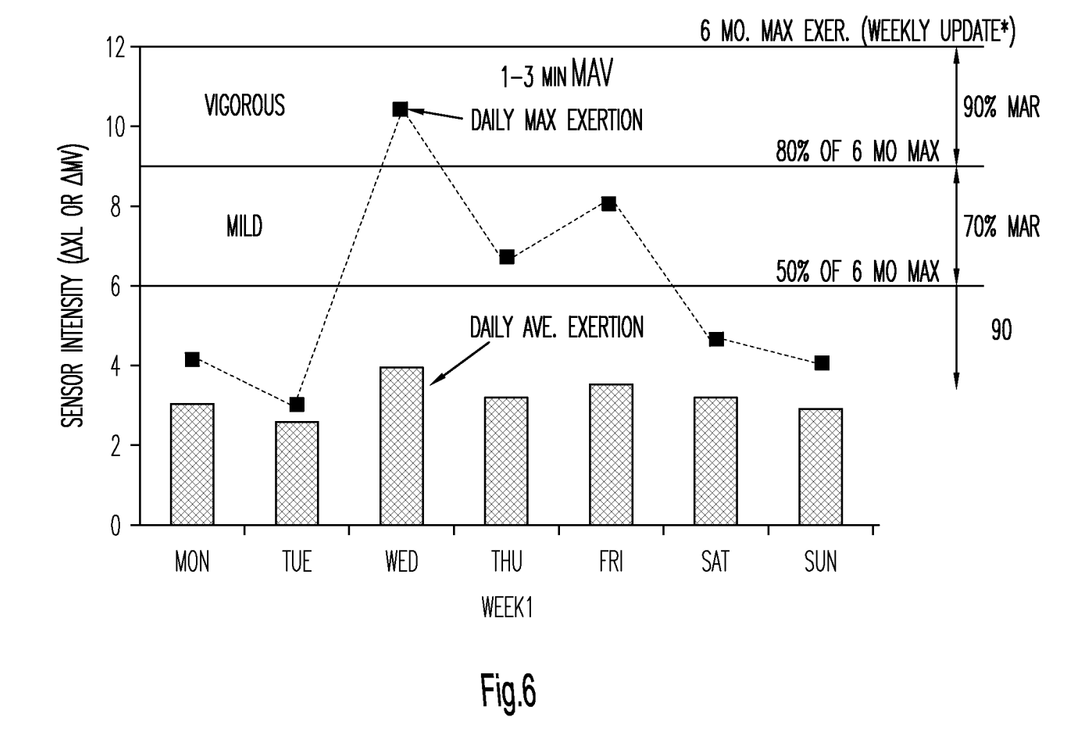
FIG. 6 shows the values of $EXL_{DailyMax}$ plotted for each day of the week and how the ranges of $EXL_{DailyMax}$ are mapped to daily maximum exertion level heart rate $EXR_{DailyMax}$ values.

FIG. 6 shows the values of $\text{EXL}_{DailyMax}$ plotted for each day of the week and an indication on the exertion level axis showing how the ranges of $\text{EXL}_{DailyMax}$ are mapped to daily maximum exertion level heart rate $\text{EXR}_{DailyMax}$ values. These values are then used to adjust the STR value in accordance with the formula given above. The daily average exertion level for each day is also shown for comparison.

As described above, the responsiveness of a rate-adaptive pacemaker depends upon four endpoint settings that define its dynamic range: the minimum pacing rate, the resting exertion level, the maximum exercise capacity or long-term maximum exertion level, and the maximum sensor-indicated rate MSR. In clinical practice, the MSR is programmed relatively low by most physicians. This is because the dynamic range of an optimized rate-response curve varies from patient to patient, and the rate-response curve may take several weeks to reach a favorable degree of responsiveness with automatic parameter adjustment as the patient's maximum exercise capacity is determined from exertion level measurements. Unless the MSR is conservatively set, the patient may experience severe overpacing during this period. Furthermore, many pacemaker patients suffer from some degree of coronary artery disease, and overpacing in this situation is especially hazardous due to an insufficient myocardial oxygen supply. A disadvantage of initially setting the MSR to a low value, however, is that the patient's exercise capacity is significantly compromised. Since the patient's maximum exercise capacity is usually mapped to the MSR by the rate response curve, the patient will never reach an appropriate paced heart rate when exercising maximally. More importantly, a low MSR will also decrease the responsiveness of the rate-adaptive pacemaker by decreasing the slope of the rate-response curve. The patient will therefore not only have a limited maximal heart rate, but will also have a lower than appropriate sensor-indicated rate beginning from exercise onset.

The under-responsiveness problem described above may be alleviated with a rate response curve that maps the long-term maximum exertion level to an age-predicted maximal heart rate or other specified maximal rate that is deemed physiologically favorable, referred to as the MAR. The specified MSR is then used only as a hard limit value for the sensor indicated rate and has no effect on the slope of the rate response curve or in the determination of the daily average maximum exertion level, long-term maximum exertion level, STR, or HRB. If the value of the MAR is less than the value of the MSR, the patient will thus never be paced at a rate corresponding to the MAR even when exercising at peak capacity. The MAR is used to establish the slope of the rate response curve so that the responsiveness of the pacemaker is not compromised by an initially low MSR value until an exertion level demanding a heart rate equal to the MSR is reached. In one embodiment, the MSR may be initially specified as a discounted percentage of the MAR and then gradually raised to the MAR over a specified length of time. For example, the MSR may be programmed as follows:

| | |
|---|---|
| First month: | MSR = LRL + 75% of (220 − age − LRL) |
| Second month: | MSR = LRL + 90% of (220 − age − LRL) |
| Third month and thereafter: | MSR = 220 - age |

The MSR can thus be set at a rate that avoids possible overpacing while the pacemaker is automatically determining the patient's maximum exercise capacity but without causing a lower than appropriate sensor indicated rate at exertion levels less than those that would be mapped to rates above the MSR.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A rate-adaptive pacemaker, comprising:
   a sensor configured to sense exertion levels; and
   a microprocessor coupled to the sensor, the microprocessor configured to:
      collect maximum exertion levels during a specified first period;
      update a maximum exercise capacity using the maximum exertion levels collected during the specified first period; and
      adjust a response factor such that the updated maximum exercise capacity is mapped to a specified maximum sensor indicated rate, the response factor being a slope of a rate response curve mapping exertion levels to sensor indicated rates.

2. The pacemaker of claim 1, wherein the microprocessor is configured to:
   collect the maximum exertion levels for specified second periods during the specified first period; and
   set the maximum exercise capacity to a maximum of the maximum exertion levels collected for the specified second periods during the specified first period.

3. The pacemaker of claim 1, wherein the sensor comprises a minute ventilation sensor.

4. The pacemaker of claim 1, wherein the sensor comprises an accelerometer.

5. The pacemaker of claim 1, wherein the rate response curve is a dual-slope curve, and the response factor changes from a low rate response factor to a high rate response factor at a heart rate breakpoint a percentage of a difference between maximum and minimum sensor indicated rates defined by the rate response curve, and the microprocessor is configured to adjust the response factor with the heart rate breakpoint maintained at a fixed percentage of the difference between the maximum and minimum sensor indicated rates.

6. The pacemaker of claim 1, wherein the rate response curve is a dual-slope curve, and the response factor changes from a low rate response factor to a high rate response factor at a heart rate breakpoint being a percentage of a difference between maximum and minimum sensor indicated rates defined by the rate response curve, and the microprocessor is configured to adjust the response factor with the heart rate breakpoint maintained at a dynamic percentage of the difference between maximum and minimum sensor indicated rates that changes with the maximum exercise capacity.

7. The pacemaker of claim 1, wherein the microprocessor is further configured to:
  collect maximum sensor indicated rates during the specified first period;
  compute an average maximum exertion level using the maximum exertion levels collected during the specified first period;
  compute an average maximum sensor indicated rate using the maximum sensor indicated rates collected during the specified first period;
  compute a sensor target rate as a function of the average maximum exertion level and the maximum exercise capacity; and
  adjust the slope of the rate response curve using the average maximum sensor indicated rate and the sensor target rate.

8. The pacemaker of claim 7, wherein the microprocessor is configured to:
  collect the maximum exertion levels for specified second periods during the specified first period;
  set the maximum exercise capacity to a maximum of the maximum exertion levels collected for the specified second periods during the specified first period;
  collect the maximum exertion levels and the maximum sensor indicated rates for specified second periods during the specified first period; and
  compute the average maximum exertion level being an average of the maximum exertion levels collected for the specified second periods during the specified first period and the average maximum sensor indicated rate being an average of the maximum sensor indicated rates collected for the specified second periods during the specified first period.

9. The pacemaker of claim 8, wherein the microprocessor is configured to adjust the slope of the rate response curve periodically using a difference between the average maximum sensor indicated rate and the sensor target rate.

10. The pacemaker of claim 8, wherein the microprocessor is configured to compute moving average values of the sensed exertion levels and moving average values of the sensor indicated rates.

11. A rate-adaptive pacemaker, comprising:
  a sensor configured to sense exertion levels; and
  a microprocessor coupled to the sensor, the microprocessor configured to:
    collect maximum exertion levels and maximum sensor indicated rates during a specified first period;
    compute an average maximum exertion level using the maximum exertion levels collected during the specified first period;
    compute an average maximum sensor indicated rate using the maximum sensor indicated rates collected during the specified first period;
    compute a sensor target rate as a function of the average maximum exertion level and a maximum exercise capacity; and
    adjust a response factor using the average maximum sensor indicated rate and the sensor target rate, the response factor being a slope of a rate response curve that maps exertion levels to sensor indicated rates.

12. The pacemaker of claim 11, wherein the microprocessor is configured to:
  collect the maximum exertion levels and maximum sensor indicated rates for specified second periods during the specified first period; and
  compute the average maximum exertion level being an average of the maximum exertion levels collected for the specified second periods during the specified first period and the average maximum sensor indicated rate being an average of the maximum sensor indicated rates collected for the specified second periods during the specified first period.

13. The pacemaker of claim 12, wherein the microprocessor is configured to compute moving average values of the sensed exertion levels and moving average values of the sensor indicated rates.

14. The pacemaker of claim 11, wherein the microprocessor is configured to adjust the response factor periodically using a difference between the average maximum sensor indicated rate and the sensor target rate.

15. The pacemaker of claim 14, wherein the microprocessor is configured to adjust the response factor in specified increments.

16. The pacemaker of claim 11, wherein the rate response curve is a dual-slope curve, and the response factor changes from a low rate response factor to a high rate response factor at a heart rate breakpoint being a percentage of a difference between maximum and minimum sensor indicated rates defined by the rate response curve, and the microprocessor is configured to adjust the low rate response factor using the average maximum sensor indicated rate and the sensor target rate.

17. The pacemaker of claim 16, wherein the microprocessor is configured to adjust the high rate response factor such that the maximum exercise capacity is mapped to a specified maximum sensor indicated rate.

18. The pacemaker of claim 11, wherein the microprocessor is configured to:
  update a maximum exercise capacity using the maximum exertion levels collected during the specified first period; and
  adjust the response factor such that the updated maximum exercise capacity is mapped to a specified maximum sensor indicated rate.

19. The pacemaker of claim 18, wherein the microprocessor is configured to:
  collect the maximum exertion levels for specified second periods during the specified first period; and
  set the maximum exercise capacity to a maximum of the maximum exertion levels collected for the specified second periods during the specified first period.

20. The pacemaker of claim 19, wherein the specified second period is a day.

* * * * *